(12) United States Patent
Speier

(10) Patent No.: US 6,518,757 B1
(45) Date of Patent: Feb. 11, 2003

(54) USE OF CPMG SEQUENCES WITH PHASE CYCLED REFOCUSING PULSES IN INSIDE-OUT NMR FOR PHASE ENCODED IMAGING AND TO ELIMINATE COHERENT RINGING WITHIN ONE SCAN

(75) Inventor: Peter Speier, Stafford, TX (US)

(73) Assignee: Schlumberger Technology Corporation, Houston, TX (US)

(*) Notice: Subject to any disclaimer, the term of this patent is extended or adjusted under 35 U.S.C. 154(b) by 0 days.

(21) Appl. No.: 10/094,564
(22) Filed: Mar. 8, 2002
(51) Int. Cl.$^7$ ................................................. G01L 3/00
(52) U.S. Cl. ...................................................... 324/303
(58) Field of Search .............................. 324/303, 307, 324/309, 300, 306, 320, 322

(56) References Cited

U.S. PATENT DOCUMENTS

| | | | |
|---|---|---|---|
| 5,023,551 A | | 6/1991 | Kleinberg et al. |
| 5,572,132 A | | 11/1996 | Pulyer et al. |
| 6,388,441 B1 | * | 5/2002 | Chen .......................... 324/303 |
| 6,429,654 B1 | * | 8/2002 | Itakovich et al. ........... 324/303 |
| 6,462,542 B1 | * | 10/2002 | Venkataramanan et al. . 324/303 |
| 6,466,013 B1 | * | 10/2002 | Hawkes et al. ............. 324/303 |

OTHER PUBLICATIONS

A. Abragam, *The Principles of Nuclear Magnetism*, Oxford University Press, pp. 34–36, 68, 86–87 (1961).
M.D. Hurlimann, "Carr–Purcell Sequences with Composite Pulses," *J. Mag. Resonance 152*, pp. 109–123 (2001).
M. Zweckstetter & T. A. Holak, "An Adiabatic Multiple Spin–Echo Pulse Sequence: Removal of Systematic Errors due to Pulse Imperfections and Off–Resonance Effects," *J. Mag. Resonance 133*, pp. 134–147 (1998).

* cited by examiner

Primary Examiner—Edward Lefkowitz
Assistant Examiner—Brij B. Shrivastav
(74) Attorney, Agent, or Firm—Kevin P. McEnaney; Brigitte L. Jeffery; John J. Ryberg

(57) ABSTRACT

A method for performing phase encoded inside-out magnetic resonance imaging. The phase of the nuclear spin is advanced by applying a magnetic field gradient between application of each of several refocusing pulse sequences so that echoes are detected during refocusing pulse sequences for different phase advances. The echoes detected for each refocusing sequence are added together and averaged. An image is then generated from the averaged echoes, such as by Fourier transform techniques. In addition, a method is provided for eliminating ringing while measuring a nuclear magnetic resonance property of a volume of earth formation surrounding a borehole. The phase of the refocusing pulses is changed so that pairs of echoes in the echo train have opposite ringing phase. Echoes in the echo train having opposite ringing phase are added to cancel ringing in the echo train. The echo train can then be analyzed for amplitude and/or decay characteristics.

34 Claims, 8 Drawing Sheets

USE OF CPMG SEQUENCES WITH PHASE CYCLED REFOCUSING PULSES IN INSIDE-OUT NMR FOR PHASE ENCODED IMAGING AND TO ELIMINATE COHERENT RINGING WITHIN ONE SCAN

BACKGROUND OF THE INVENTION

1. Field of the Invention

The present invention relates to inside-out (I/O) nuclear magnetic resonance (NMR) imaging techniques, and more particularly to a method for cancelling coherent ringing within an echo train and a method for phase encoded imaging under I/O conditions.

2. Description of the Related Art

In recent years, I/O NMR has become an increasingly important measurement technique for oilwell logging and has lately been applied also in other contexts like material research applications. Inside-out NMR is different from conventional NMR spectroscopy and imaging insofar as the investigated sample is outside the spectrometer, not in the center of a polarizing magnet. Therefore the applied magnetic fields, the static polarizing field and the oscillating or radio frequency (RF) field, are by no means homogeneous. From the point of view of the measurement the sample is infinite, and the spatial center of the volume, which contributes useful signal (henceforth called the resonance volume), is given by the points where $\omega_{rf}=\gamma B_0$. Here, $\omega_{rf}$ is the carrier frequency of the RF pulses, and $\gamma$ is the gyromagnetic ratio of the nuclei under investigation. The boundaries of the resonance volume are given roughly by the condition $|B_0-\omega_{rf}/\gamma|<B_1$. Therefore the spectral width of the signal that is measured in an I/O NMR experiment is always of the order of $\gamma B1$, except if it is reduced by using a frequency limiting detection filter. This means that frequency resolved information like chemical shifts cannot be obtained, and measurements are restricted to measurements of relaxation times, diffusion, flow, etc.

In logging applications, these measurements are made with (sets of) Carr-Purcell-Meiboom-Gill (CPMG) refocusing pulse sequences. The CPMG sequence invokes large off resonance and pulse flip angle error correction capabilities and is thus useful to conserve the signal in a large region surrounding the resonance condition. This characteristic is prerequisite for detecting the "true" decay rate of the echo train;.otherwise the observed decay rate will be shortened and possibly dominated by a sequence dependent decay rate. Two CPMG measurements with inverted excitation pulse phases are generally combined to cancel NMR baseline effects and coherent ringing from the refocusing pulses. The result is what is called a phase alternated pair (PAP), disclosed in U.S. Pat. No. 5,023,551.

In the 1980's, a class of multi-echo sequences was developed for NMR spectroscopy and imaging applications in which the phases of successive refocusing pulses are cycled. These are called phase cycled CPMG (PCCPMG) sequences. The group consists of two subgroups: sequences with a nucleus of 90 degree phase shifts between consecutive echoes (XY4, XY8, XY16), and the MLEV sequences with 180 degree phase shifts between consecutive echoes (MLEV4, MLEV8, MLEV16). Another CPMG type sequence, the Freeman Hill modification of CPMG (+x[−x+x]), performs under I/O NMR conditions almost exactly like CPMG. The PCCPMG sequences have an advantage over CPMG that the PCCPMG sequences conserve all components of the magnetization. They achieve this by canceling the spin rotations introduced by the preceding pulses by subsequent pulses within a cycle. The result is that the magnetization vector after a full cycle returns approximately to its original direction for a wide variety of conditions. By contrast, during CPMG sequences, the spin vector is always rotated around the save axis through the same angle. Thus, CPMG sequences conserve only one component of the transverse magnetization. The other component is rapidly uniformly distributed. Compared to CPMG, PCCPMG sequences conserve less signal bandwidth. Nevertheless, it has been shown that a PCCPMG sequence with 90 degree phase shift (XY16) can be used under I/O NMR conditions to measure T2 without spin locking effects that had been observed when using CPMG.

Recently, phase encoded imaging was demonstrated under I/O NMR conditions using a single echo sequence. True phase encoded imaging relies on the phase of the signal being proportional to the applied gradient. This is certainly true for the first echo under I/O conditions. It is not true for further CPMG echoes, since only one magnetization component is conserved.

There is room for improving NMR imaging techniques useful under I/O conditions.

SUMMARY OF THE INVENTION

Briefly, a method is provided for performing phase encoded inside-out magnetic resonance imaging. A static magnetic field is applied to a volume of an earth formation surrounding a borehole that polarizes the nuclear spin within the volume of earth formation. An excitation pulse is applied into the formation that rotates nuclear spin from a longitudinal axis of the static magnetic field to a plane transverse thereto. A sequence of refocusing pulses is applied a period of time after termination of the excitation pulse to generate a plurality of echoes. The echoes induced by the refocusing pulses are detected. Next, the magnetic field is altered such that for a period of time, the strength of the magnetic field in the volume is spatially dependent, thereby inducing a magnetic field gradient in the earth volume that advances the phase of the nuclear spin. The refocusing pulse sequence is run again after the phase advance to detect more echoes, and this process is repeated for further phase advances so that a refocusing sequence is run for each of several phase advances. The echoes detected for each refocusing sequence are added together and averaged. An image is then generated from the averaged echoes, such as by Fourier transform techniques. As a variation, the phase advance is applied after the excitation pulse and before the first refocusing pulse sequence. Several refocusing sequences are run with that phase advance. Then, after a waiting period to allow for repolarization, another excitation pulse is applied, and the process is repeated with another phase advance. It is also possible to combine these two phase processes, where the direction of the magnetic field gradients applied in each would be different.

In addition, a method is provided for eliminating ringing while measuring a nuclear magnetic resonance property of a volume of earth formation surrounding a borehole. An excitation pulse is applied into the formation that rotates the nuclear spin from a longitudinal axis of the static magnetic field to a plane transverse thereto. A sequence of refocusing pulses is applied a period of time after termination of the excitation pulse to generate a plurality of echoes. The phase of the refocusing pulses is changed so that pairs of echoes in the echo train have opposite ringing phase. The echoes are detected. Additional sequences of refocusing pulses are applied to generate more echoes. Echoes in the echo train having opposite ringing phase are added to cancel ringing in the echo train. The echo train can then be analyzed for amplitude and/or decay characteristics.

DETAILED DESCRIPTION OF THE INVENTION

For a CPMG refocusing pulse sequence under I/O NMR conditions, the spin component orthogonal to the effective rotation axis from echo to echo is distributed randomly. Only the projection of the echo on this effective rotation axis is conserved. Therefore, if successive phase shifts in the spin magnetization are introduced during the echo train, this leads to rapid decay of the NMR signal instead of the gradient dependent modulation of the echo train that is necessary for phase encoded imaging. Thus, true phase encoded imaging is not possible with a CPMG refocusing sequence under inside-out conditions since it requires to advance the phase of the NMR signal between detection points.

The PCCPMG sequences conserve all three components. Such sequences allow introduction of phase shifts into the echoes between the refocusing sequences (also called "building blocks") without losing one component of the signal. Therefore the phase of the echoes can be advanced as required by phase encoded imaging, e.g., using a gradient field.

Figure 1:
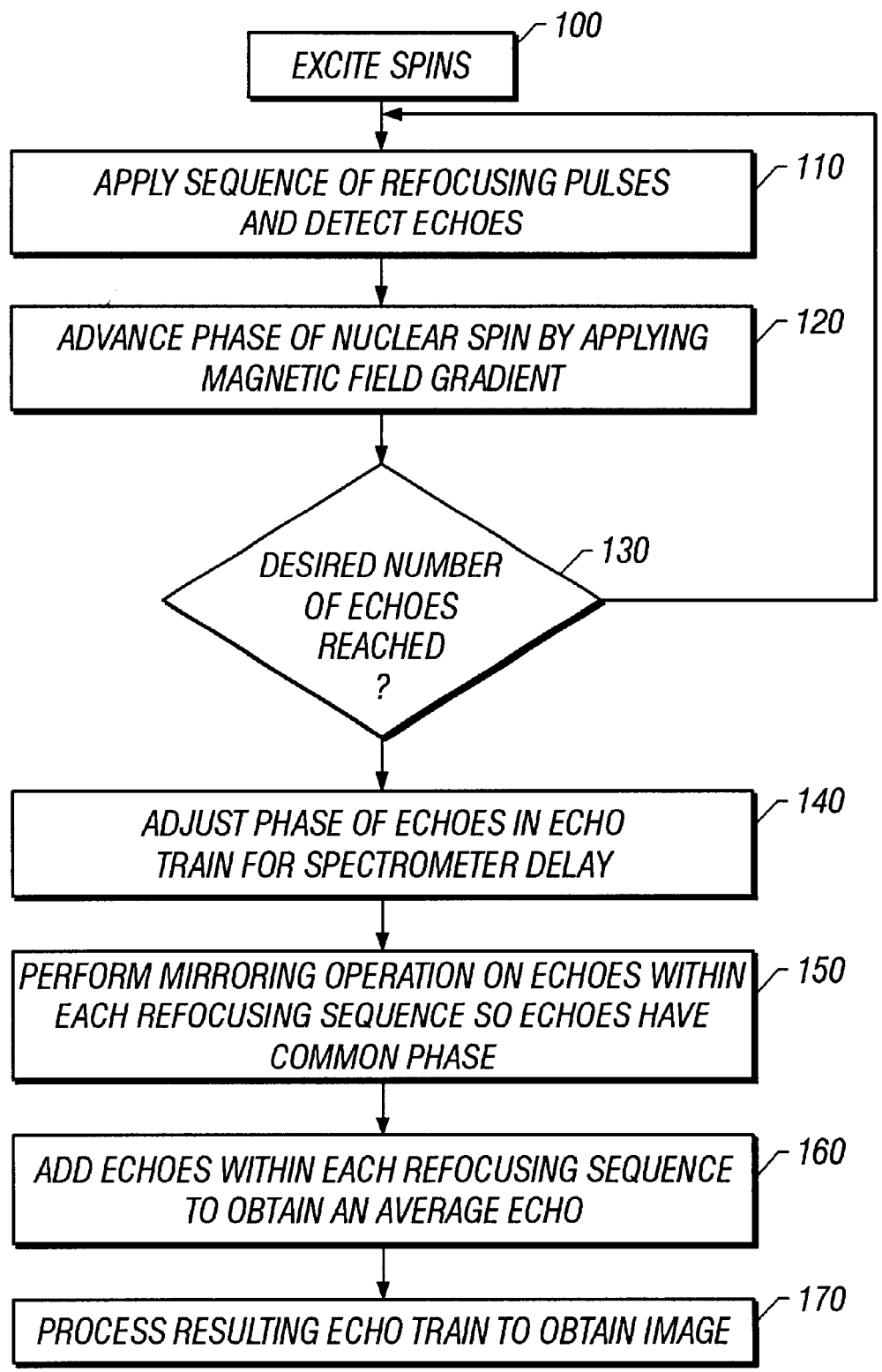
FIG. 1 is a flow chart showing a process for phase encoded inside-out phase encoded NMR imaging according to one aspect of the invention.

Referring first to FIG. 1, a process is described for performing phase encoded I/O NMR imaging. Initially, and not specifically shown in FIG. 1, a static magnetic field is applied to a volume of an earth formation surrounding a borehole which polarizes the nuclear spin within the volume of earth formation. This step will establish a magnetic field gradient in the volume, and is well known in the art of NMR imaging. Next, in step 100, an excitation pulse is applied into the formation that rotates the nuclear spin from a longitudinal axis of the static magnetic field to a plane transverse thereto. Again, step 100 is well known in the art. Next, in step 110, a sequence of refocusing pulses are applied a period of time after termination of the excitation pulse to generate a plurality of echoes, and the echoes from the formation induced by each pulse in the sequence of refocusing pulses are detected. In step 120, the phase of the nuclear spin in the earth formation is advanced by applying a magnetic field gradient pulse. This is achieved by altering the magnetic field in the volume (using a gradient coil configuration) such that for a period of time, the strength of the magnetic field in the volume is spatially dependent. Generally, the magnetic field gradient is applied in a direction that is substantially orthogonal to the direction of the gradient of the static magnetic field referred to above prior to step 100. Steps 110 and 120 are repeated until a desired number of echoes are obtained, as indicated in step 130. Thus, a refocusing sequence is applied to the formation for each of the phase advances, resulting in a sequence of echoes associated with the different phases, consistent with a phase encoded imaging process.

Once the desired number of echoes are obtained by cycling through steps 110 and 120 numerous times, in step 140, the phase of the echoes is adjusted for spectrometer delay between application of the refocusing pulse and detection of the subsequent echo. This phase correction depends primarily on the bandpass characteristics of the transmitting and receiving system. The value of this phase correction can be determined either using measurements or using surface calibration data extrapolated to downhole conditions.

Next, in step 150, a mathematical operation, hereinafter called a mirroring operation, is performed on the echoes associated with each refocusing sequence so that the echoes for that refocusing sequence have a common phase. The operation in step 150 may involve projecting each echo about one or more coordinate axes in the transverse plane (x-axis and/or y-axis) so that all the echoes obtained from a refocusing sequence have a common phase. Here, the axes correspond to the RF carrier phases of the applied RF pulses.

The echoes for a refocusing sequence now have a common phase and the common phase echoes for each refocusing sequence are added together in step 160 to generate an average echo for each refocusing sequence. Thus, assuming that numerous refocusing sequences have been applied, there would be an average echo for each refocusing sequence, resulting in an echo train. This echo train of average echoes is processed in step 170 to obtain the image. One type of processing that can be performed in step 170 is Fourier transformation of the echoes.

Figure 2:
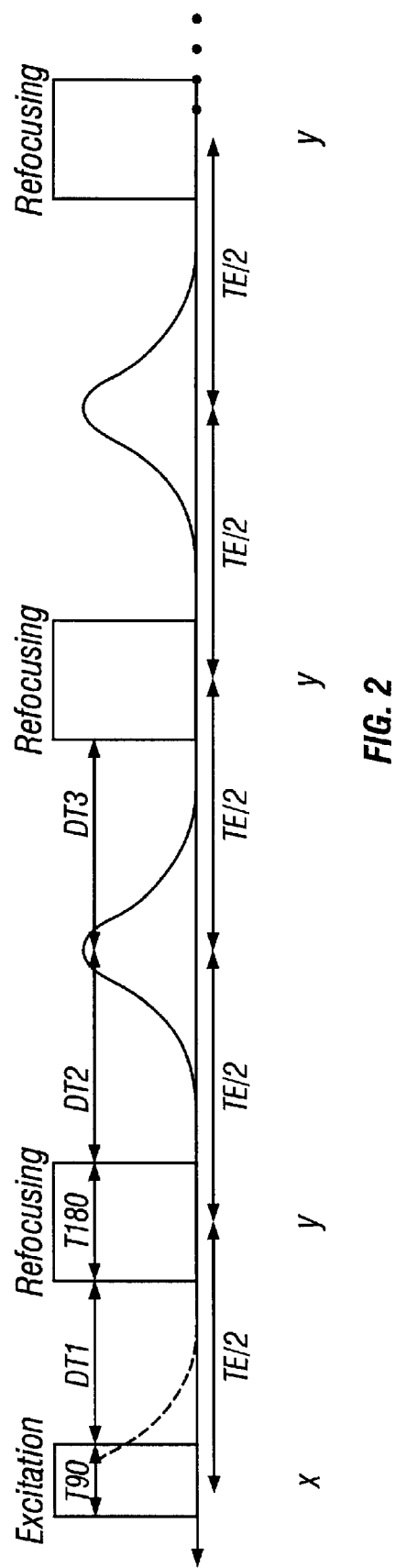
FIG. 2 is a timing diagram of an echo sequence useful in the imaging process of FIG. 1.

A further explanation of the physical events that occur during the process of FIG. 1 is provided with reference to FIG. 2. The timing scheme in steps 100 and 110 is the same as for a CPMG sequence. The sequence starts with an excitation pulse in step 100, also called a 90 degree pulse, of duration T90. This excitation pulse rotates the spins from the longitudinal axis (parallel to $B_0$) into the transverse plane. After a time DT1 a refocusing (or 180 degree pulse) of duration T180 is fired. After the pulse an echo starts to build up in the receiver. It reaches maximum amplitude after another time DT2. At a time DT3 after the echo maximum is detected, the next refocusing pulse is fired and the sequence continues with the same timing for the rest of the echoes. The echoes are separated by a time period TE from each other.

The following timings provide maximum signal for rectangular pulses:

DT1=TE/2–T180/2–2/π*T90.

DT2=TE/2–T180+DTS

DT3=TE/2–T180–DTS, where DTS is the spectrometer transmit and receive delay. T90 and T180 are determined by signal maximization as usual, since the pulse flip angles vary over the resonance volume (due to both $B_0$ and $B_1$ variations).

Echoes are usually detected using echo integration with a detection filter matched to provide optimum SNR (between 1 and 2 $B_1$ wide). For in slice imaging, echoes shapes can be detected with a broadband filter. A fast Fourier transform of the echo will then result in an image along the slice.

The timing above is for rectangular pulses with constant phases. The timing will slightly change if rise and fall time become finite due to the band pass characteristics of the transmitting circuits and can be determined numerically or optimized using measurements.

Each refocusing pulse above can be substituted with a composite pulse sequence known in the art, such that each refocusing pulse comprises a composite pulse sequence composed of multiple pulses in a row. Many pulses are possible, as, e.g., described with respect to CPMG in M. D. Hurlimann, "Carr-Purcell Sequences with Composite Pulses", *J. Magn. Reson.* 152, p.109–123 (2001).

Furthermore, the excitation pulse can be substituted with an adiabatic half passage pulse. Both composite pulses and adiabatic passages can increase the effective bandwidth with respect to $B_0$ and/or $B_1$ of the basic sequence and thus the amplitude of the received echo. Adiabatic pulses, used since the 1950s in NMR and described, e.g., in A. Abragam: Principles of Nuclear Magnetism, Oxford, 1961, are pulses that change at least the frequency of the carrier in a slow continuous fashion so that the spins can adjust and follow the changing resonance condition or, in NMR terms, the effective field. This implies that the pulse must start sufficiently far from the resonance (in frequency space). By sweeping adiabatically through a resonance, completing the full passage in a time shorter than the relaxation times, the spin vector can be inverted. However, when inverting transverse magnetization as one does when refocusing echoes, the adiabatic inversion introduces a phase shift in the transverse spin components depending on the resonance frequency of the inverted spin. To form an echo train, this phase shift must be cancelled by applying several passages, e.g., as described in M. Zweckstetter and Tad A. Holak, "An Adibiatic Multiple Spin-Echo Pulse Sequence: Removal of Systematic Errors due to Pulse Imperfections and Off-Resonance Effects," *J. Magn. Reson.* 133, p. 134–147 (1998).

The adiabatic half passage is simply the first half of an adiabatic fast passage that starts far from the resonance and ends exactly in the resonance. Like a 90 degree pulse, this results in transverse magnetization that can be observed, e.g., using an echo train. Excitation by adiabatic half passage can be advantageous, e.g., in cases where $B_1$ is very inhomogeneous and the flip-angle of 90 degree can be achieved only in a fraction of the sample. Alternatively to changing the carrier frequency of the RF pulse, one can sweep the DC magnetic field to produce adiabatic changes.

With reference to FIG. 2 each RF pulse has a phase. For simple pulses this is the difference of the phase of the pulse carrier signal and a reference signal. For composite and adiabatic pulses this is the phase of the axis of the effective rotation that is created by the pulse near optimum conditions, i.e., in resonance and at nominal $B_1$.

The pulse phases for a CPMG refocusing sequence are shown in FIG. 2 as an example: excitation=x, refocusing=y. Thus, the CPMG sequence can be abbreviated as x yyy . . . or shorter x[y]. An example for a XY4 sequence is x xyxy xyxy . . . or x[xyxy]. An example for a XY16 sequence is x[+x,+y,+x,+y, +y,+x,+y,+x, -x,-y,-x,-y, -y,-x,-y,-x].

Figure 3:
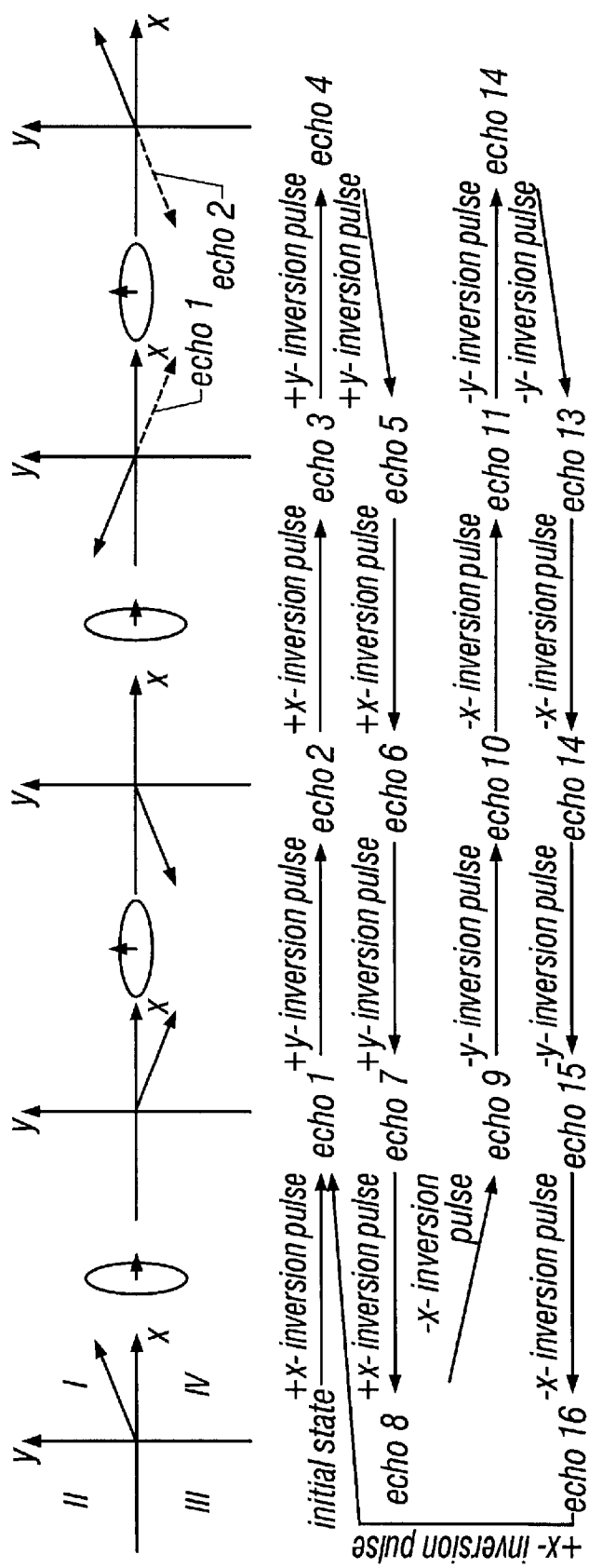
FIG. 3 is a diagram showing orientation of the magnetization vector associated with the different echoes in the transverse plane.

FIG. 3 shows the orientation of the magnetization vector at the time of the different XY8 (or if continued for 8 more echoes, and XY16 sequence) echoes in the transverse plane. Between echoes, refocusing pulses are applied. The rotation planes of these pulses are shown as the shaded circles. The x and y axes of the coordinate system are defined by the pulse phases (0 and 90 degree in polar coordinates). The polar angle of the magnetization vector at the time of the echo is also called the phase of the echo.

Below the figures, an XY8 phase cycle is shown. It starts with the initial state before the first pulse of the cycle. For the first cycle in a sequence this initial state is unobservable because it is within the excitation pulse. The spins are inverted with an x pulse, which creates 180 degree rotation around the x axis. Echo 1 is formed in quadrant 4. Next, the spins are inverted with a y pulse, which creates 180 degree rotation around the y axis. Echo 2 is formed in quadrant 3. The spins are inverted with an x pulse, which creates 180 degree rotation around the x axis. Echo 3 is formed in quadrant 2. The spins are inverted with a y pulse, which creates 180 degree rotation around the y axis. Echo 4 is formed in quadrant 1. The spins are inverted with a y pulse, which creates 180 degree rotation around the y axis. Echo 5 is formed in quadrant 2. The spins are inverted with a x pulse, which creates 180 degree rotation around the x axis. Echo 6 is formed in quadrant 3. The spins are inverted with a y pulse, which creates 180 degree rotation around the y axis. Echo 7 is formed in quadrant 4. The spins are inverted with a x pulse, which creates 180 degree rotation around the x axis. Echo 8 is formed in quadrant 1. For an XY16 sequence, the entire process is repeated again, with inverted phase pulses.

During the last free evolution t_cp* period after the detection of the last echo in the refocusing sequence, the magnetic field gradient is applied (step 120) for a time duration that introduces a position dependent phase shift dph(x), where x is the coordinate along which the gradient field varies in the resonance zone. Again, the phase of the echoes may be adjusted for spectrometer delay between application of the refocusing pulse and detection of the subsequent echo. This phase correction depends primarily on the bandpass characteristics of the transmitting and receiving system. The value of this phase correction can be determined either using measurements or using surface calibration data extrapolated to downhole conditions.

In order to adjust echoes 1–8 to have a common phase, their projections onto the x-axis and y-axis have to be multiplied with the following signs. This effectively performs the mirroring operation(s) about the x-axis and/or y-axis in the transverse plane according to the phase of the refocusing pulses so that all the echoes obtained from a refocusing sequence have a common phase for that refocusing sequence. This corresponds to the processing step 150 of FIG. 1.

|  | X | Y |
| --- | --- | --- |
| Echo 1 | + | − |
| Echo 2 | − | − |
| Echo 3 | − | + |
| Echo 4 | + | + |
| Echo 5 | − | + |
| Echo 6 | − | − |
| Echo 7 | + | − |
| Echo 8 | + | + |

Referring back to FIG. 1, for detection, the echoes within each block or refocusing sequence are added and averaged in step 160 to form a block echo BE. The train of block echoes BE is then Fourier transformed to yield an image with respect to the gradient distribution in step 170. The spins at position x contribute to intensity at the frequencies dph(x)/(2$t_b$), where $t_b$ is the duration of a refocusing sequence or building block. In the case of XY8, $t_b$=8*$t_e$=16*$t_{cp}$. If dph(x) is proportional to x, the image is easy to interpret. Since primarily only the magnetic field component of the gradient that is parallel to $B_0$ is effective, this simple case is hard to achieve except in special cases such as, e.g., axial $B_0$ and axial imaging, where an axial anti-Helmholtz coil could produce a substantially linear axial gradient in an extended volume in the formation. In other cases a deconvolution procedure is useful. To resolve ambiguities, it may be appropriate to merge two experiments, e.g., one with dph(x)=A cos(x) and one with dph(x)=A sin(x) for azimuthal imaging.

Phase encoded echo train imaging is especially useful for porosity or free fluid imaging (with associated long T2s) since the achievable imaging resolution decreases with increasing decay rate of the echoes. Since for a $B_0$ gradient tool, the radial thickness of the shell is negligible against the other shell dimension, it is easier to dephase or phase-encode axially or along the circumference than radially. In the logging application, azimuthal imaging for axisymmetric tools facilitates detection of bed directions and dip angles. Axial imaging can be used to enhance the vertical resolution of long antennae without increased speed effect on the signal decay in relaxation measurements that a shortened coil would be subject to. Thus, the need for a second coil for high resolution measurements is eliminated. Radial images can be obtained by varying the operating frequency $\omega_{rf}$.

Figure 4:
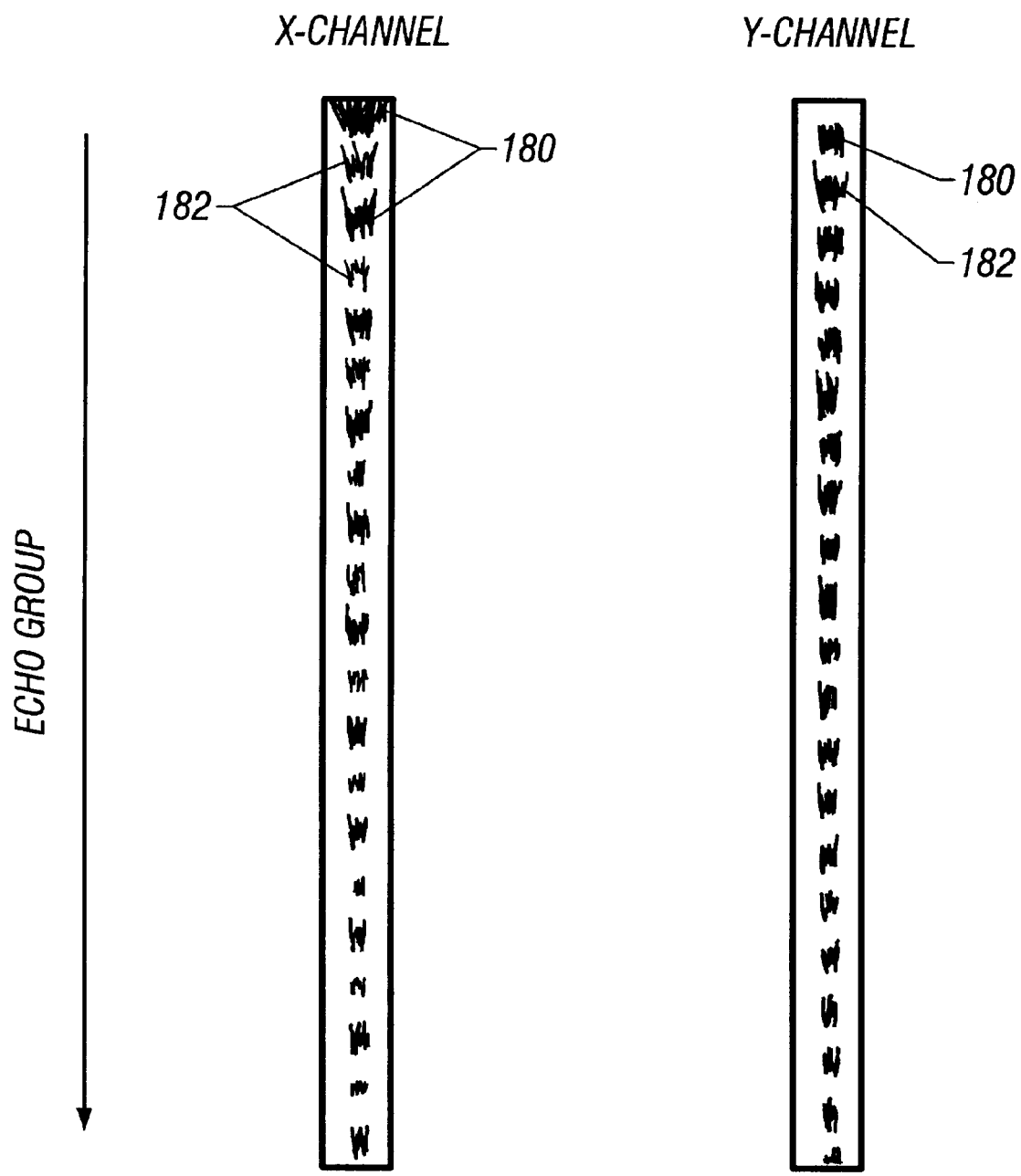
FIG. 4 is a graphical diagram showing frequency resolved echo trains recording with an Y[XY8] sequence employing phase-encoded NMR imaging procedures.

With reference to FIG. 4, the suitability of the XY8 sequence as an example for PCCPMG sequences in inside out NMR conditions is shown by the following numerical spin dynamics simulation results. The simplified field geometry was a constant gradient in B0 and a constant value for B1. A Y[XY8] sequence was run as before, and in each period t_cp*, after recording the last echo of each block, a 30 degree phase shift was introduced in the spin magnetization to simulate the effect of a gradient pulse. The image is divided in two parts: The lefthand side shows the signal in the x-channel and the righthand side shows the signal in the y-channel. The responses from successive echo groups are plotted from top to bottom. The frequency resolved signal is plotted along the horizontal axis. The resonance condition is exactly fulfilled in the center columns. The alternating shaded areas 180 describe positive signal and the alternating shaded areas 182 describe negative signal. The larger the amplitude, the heavier the shaded area. The net signal is concentrated in a small stripe around the center frequency. The signal in the top row is the signal of the first echo group. Its width corresponds roughly to the width of a CPMG echo.

Following the signal through the successive groups (top to bottom), the signal decays slowly, with the frequency components farthest off resonance, that originate near the radial limits of shell, decaying fastest. The decay eventually slows down and seems to reach an equilibrium state at about half the original signal width. This signal then is conserved. By reducing the receiver bandwidth, and thus sacrificing initial signal-to-noise, this initial decay can be rendered invisible. Using a higher phase cycle like XY16 also reduces the initial decay rate; however, a cycle of this sequence is twice as long, and thus reduces by one-half, the number of points that can be sampled for a given T2.

Besides the signal conservation, it is important to note that the signal in the region that is finally conserved, is rotated uniformly, i.e., the frequency components keep their phase relationship. Counting the number of group echoes per period, it is evident, that the signal indeed is rotated by 30 degrees every group. Thus, at least the XY8 sequence of the PCCPMG family is useful for phase encoded imaging under I/O NMR conditions.

Figure 5:
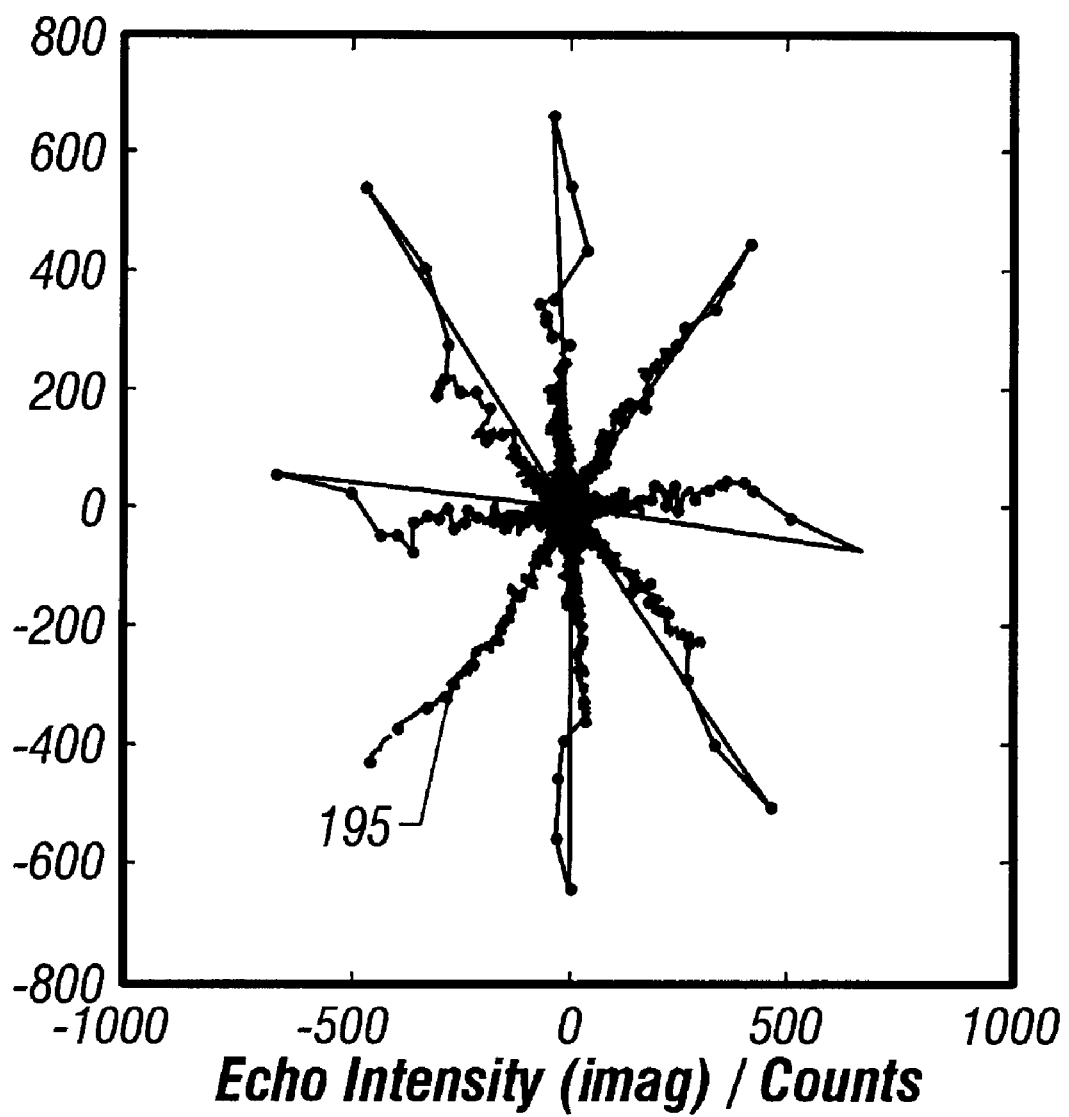
FIGS. 5–7 are graphical diagram showing experimental results for an XY8 pulse sequence in an I/O synthetic phase encoded NMR imaging process.

FIG. 5 shows the performance of the XY8 sequence with an I/O NMR gradient setup with both B1 and B0 inhomogeneity. The complex echo amplitudes are plotted in the transverse plane for eight different excitation phases (0, 45, 0, . . . degrees) without gradient application. Points belonging to the same echo train are connected. Within an echo train the points progress from the outside towards the origin of the plot as the echo amplitude decays. The phase of the signal is conserved approximately independent of the phase of the excitation pulse. This corresponds to the fact that both transverse components of the magnetization are conserved approximately with the same efficiency. The trace indicated at reference numeral 195 is a signal during one echo sequence and has constant phase (phase is conserved) as no gradient is applied.

This phase conservation is useful to perform phase encoded imaging with a phase encoded gradient pulse between the refocusing sequences, as shown in FIG. 1. If a magnetic field gradient is applied with the same duration and amplitude for each refocusing sequence, the phase for each voxel is always advanced by the same phase from refocusing sequence to refocusing sequence. Taking the resulting echo train as a vector of sampling points, this creates a frequency encoding of the voxel. A fast Fourier transform (FFT) along the echo train yields an image with the contributions sorted according to the gradient integral they experience. The XY8 refocusing sequence produces echoes with several phases. Thus, before applying the FFT, these echoes are phase-corrected and added. Alternatively, spectrum can be created using only a subset of echoes, e.g., for XY8, every $8^{th}$ echo.

Figure 6:
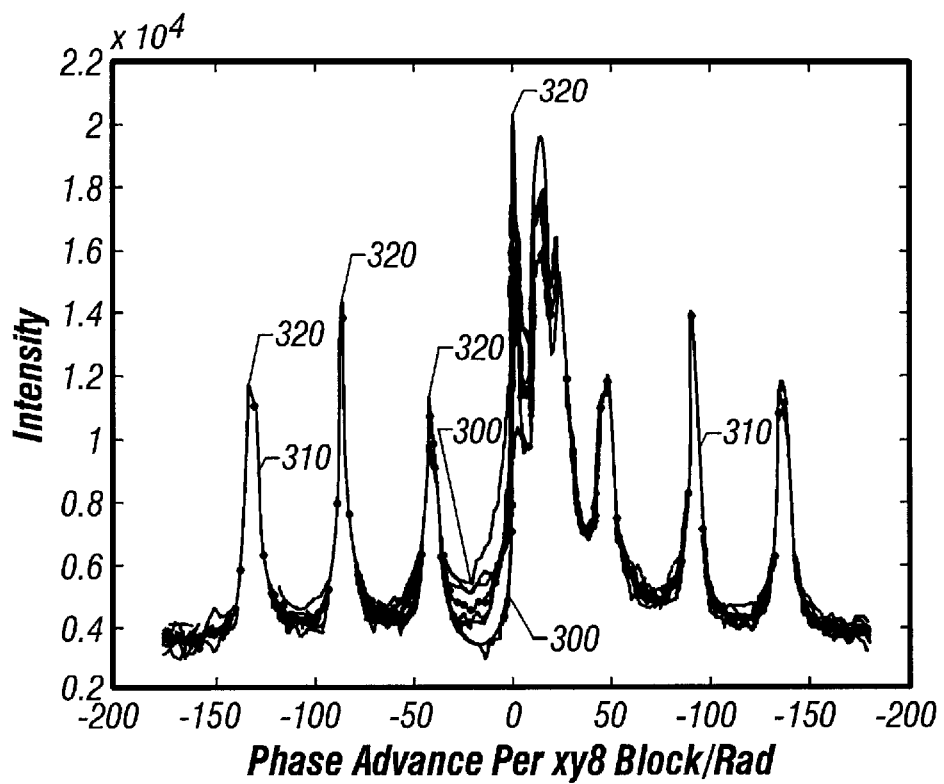
Figure 7:
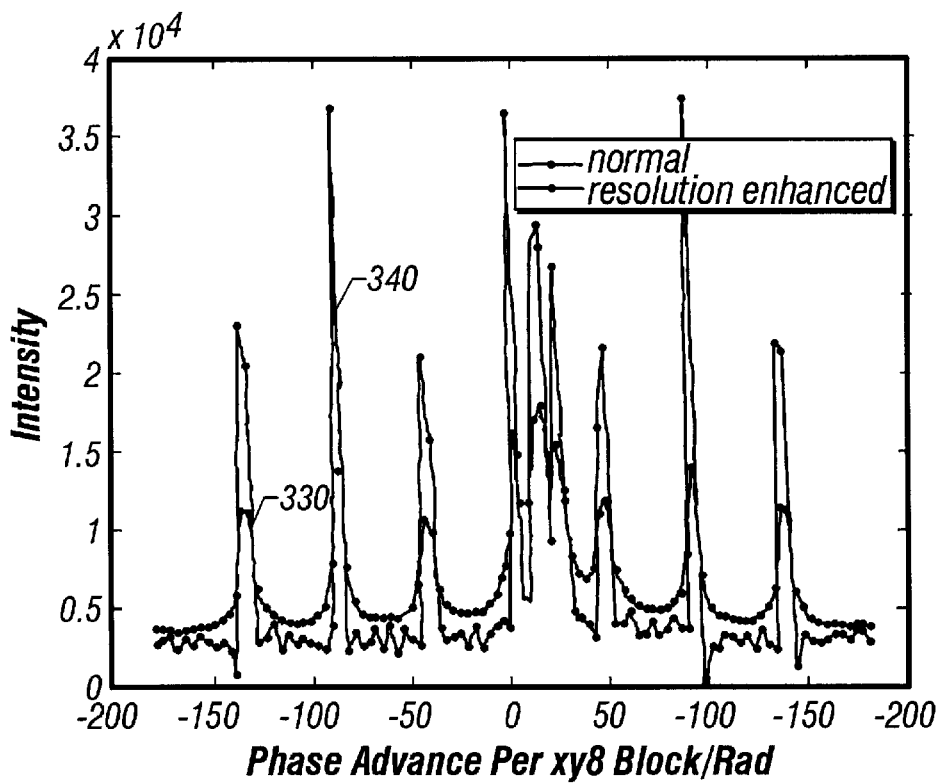

FIGS. 6 and 7 show experimental data for a synthetic image produced using a phase-encoded process in the same I/O NMR gradient setup as above. This image was created using an XY8 sequence and a homogeneous water sample. In order to generate the data shown in FIGS. 6 and 7, the frequency encoding was created artificially by advancing the phase of the pulses and receiver subsequent XY8-blocks by a constant phase. This is equivalent to the pulses and receiver having a constant phase and the spins being advanced in the opposite direction (with the exception of slight pulse integral variations caused by forcing pulses with different phases on a Larmor grid). The phase advances were 0, 45, 90, 135 and 180 degrees. In the Fourier spectrum, a phase advance of 180 degrees per point corresponds to the Nyquist frequency, and thus to 0 degrees. Since the phase resolution of the spectrometer was 45 degrees, advance angles of 45/N degrees were approximated by advancing the phase only every Nth XY8-block. In this way, the angles (11.5, 15 and 22.5 degrees) were created. The echo trains for the different phase advances were summed up. The resulting phase corrected absorption spectrum is shown in FIG. 6.

In FIG. 6, the fainter lines 300 show the spectra created with different phases for the excitation pulse. The solid black lines 310 with dots show the average of these spectra and corresponds to an averaging phase cycle over these excitation phases. Each peak 320 is created by a different phase advance angle. The differences in amplitude and shape are due to differences in the conservation efficiency of XY8 for the two transverse spin components. Since this efficiency is known and depends only on the excitation phase and phase advance angle, it is possible to compensate for it to create a perfect image. FIG. 7 shows the same data in FIG. 6 with resolution enhancement, by multiplying the echo train before the FFT with a filter function that increases monotonically with echo number. The fainter line 330 is without resolution enhancement and the darker line 340 is with resolution enhancement.

There are many variations to the phase encoded I/O NMR imaging process of FIG. 1. The step 120 of advancing the phase of the nuclear spin normally comprises applying a magnetic field of a magnitude and time duration suitable to advance the phase of the nuclear spin by substantially the same amount for each refocusing pulse sequence. However, the phase advance amount can be different from refocusing sequence to refocusing sequence, by changing either the gradient magnitude or the time duration of the gradient. An additional magnetic field of a gradient magnitude and a time duration may be applied in a direction different from a direction of the magnetic field gradient applied in step 120. This additional magnetic field may be applied before step 110 of applying the refocusing pulse sequences.

The sequence of refocusing pulses applied in step 110 may be a sequence of phase cycled CPMG refocusing pulses, such as the XY8 sequence. Moreover, each refocusing pulse may be a composite pulse sequence, wherein the composite pulse sequence comprises multiple pulses.

Still another variation is to advance the phase of the nuclear spin after application of the excitation pulse and before application of the refocusing pulse sequences. Thus, the phase advance would be applied once, and thereafter multiple refocusing sequences would be applied to generate a suitable number of echoes for that phase advance. Then, the entire process is repeated whereby after a wait time sufficient for repolarization, an excitation pulse is applied, a new phase advance is applied, and echoes are generated with refocusing pulse sequences. This would be repeated for several phase advances until a desired number of phase advances are obtained. Steps 140 through 160 are performed for the echoes generated at each phase advance to obtain average echoes for each refocusing sequence (at each phase advance). An image is then generated from the average echoes obtained at each phase advance. In this variation, the multiple average echoes would be first obtained for the same phase advance, which are then combined with subsequently obtained average echoes for the further phase advances. Enhancements to this variation include applying an additional magnetic field to the formation of a magnitude and a time duration to create a magnetic field gradient in a direction different from the direction of the other magnetic field gradient. This additional magnetic field gradient may be applied after completion of a refocusing sequence and before applying the next refocusing sequence.

Figure 8:
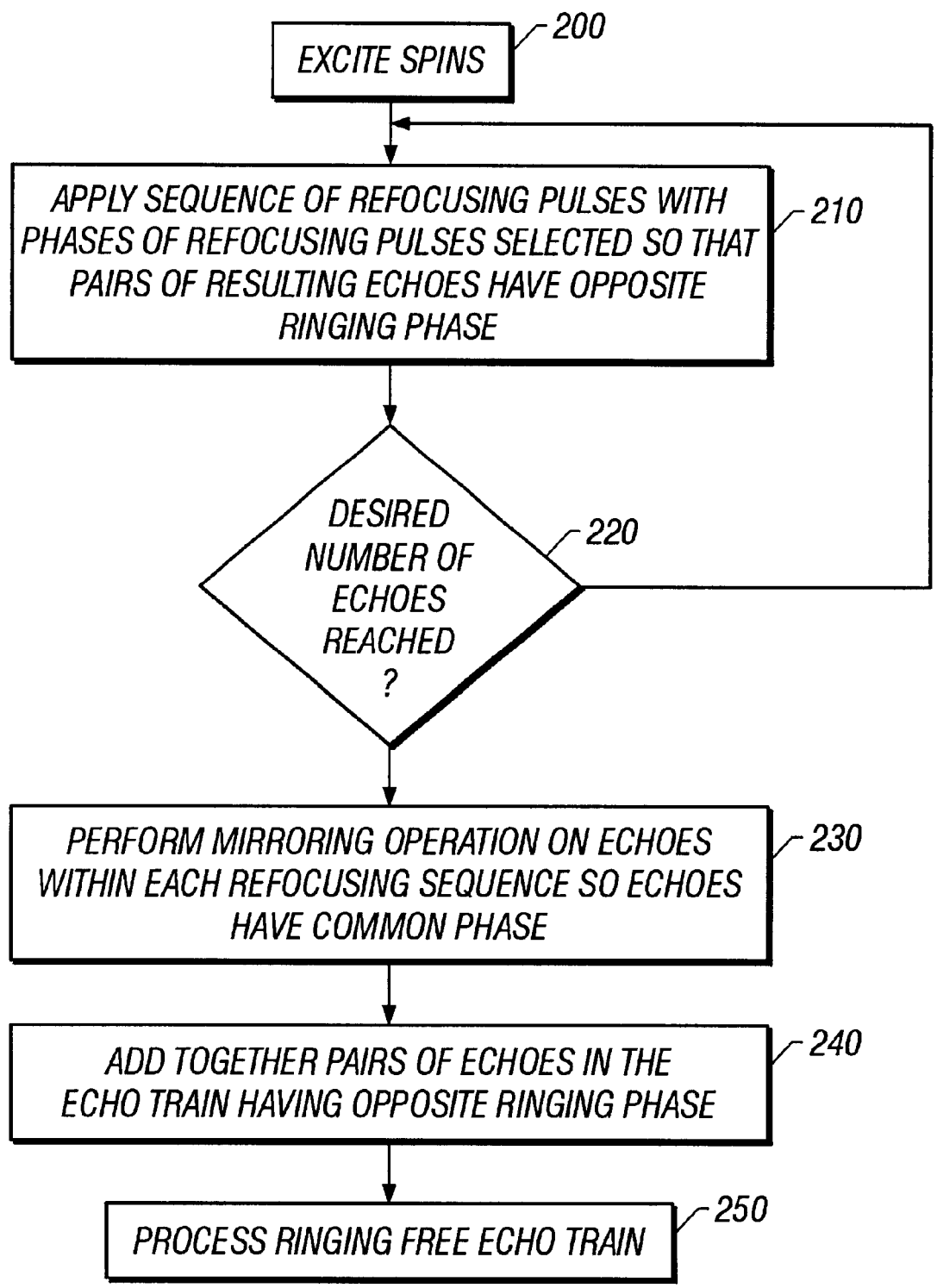
FIG. 8 is a flow chart showing a process for eliminating coherent ringing between echoes in a single scan.

Referring now to FIG. 8, a process for eliminating coherent ringing between echoes in an echo train is described. Many of the steps in FIG. 8 are similar to steps in FIG. 1. Initially, a static magnetic field is applied in the volume of an earth formation surrounding a borehole that polarizes the nuclear spin within the volume. In step 200, an excitation pulse is applied into the formation that rotates the nuclear spin from a longitudinal axis of the static magnetic field to a plane transverse thereto. In step 210, a sequence of refocusing pulses is applied a period of time after termination of the excitation pulse to generate a plurality of echoes. In step 210, the phase of the refocusing pulses within a refocusing sequence are changed or selected so that pairs of echoes in the resulting echo train have opposite ringing phase. The echoes forming this pair may appear in any order in the echo train. For example, in an XY8 sequence, the echo pairs are (1, 3), (2, 4), (5, 7) and (6, 8). More specifically, the phase of the refocusing pulses are changed so that the angle between an echo vector and the rotation axis of its preceding refocusing pulse is in an opposite quadrant with respect to the angle between a subsequent echo vector and its preceding pulse. In other words, the echo vectors of interest point are in opposite quadrants and point in completely opposite directions, i.e., they are diametrically opposite.

In step 210, the echoes induced by the refocusing sequence are detected. In step 220, additional sequences of refocusing pulses are applied until a desired number of echoes are obtained. The phase of the echoes may be adjusted for spectrometer delay between application of the refocusing pulse and detection of the subsequent echo. This phase correction depends primarily on the bandpass characteristics of the transmitting and receiving system. The value of this phase correction can be determined either using measurements or using surface calibration data extrapolated to downhole conditions. In step 230, for each echo, at least one mirroring operation about at least one axis in the transverse plane is performed according to the phase of the refocusing pulses so that all the echoes obtained from a refocusing sequence have a common phase for that refocusing sequence. This is very similar to step 150 of FIG. 1. Next, in step 240, echoes in the echo train that have opposite ringing phase are added together to cancel ringing. The echoes that are added may result from pulses in one refocusing sequence, or from pulses that span from one refocusing sequence into another. This would depend on how the phases of the refocusing pulses are selected or changed. In step 250, the resulting echo train is analyzed for amplitude and/or decay characteristics.

With reference to FIG. 3, in conjunction with FIG. 8, the phase relationship between certain echo vectors and their preceding refocusing pulses necessary to achieve echoes of opposite ringing phase (thereby enabling ringing cancellation), will be described further. Ringing cancellation between two echoes occurs because the angle between an echo vector and the pulse rotation axis of the refocusing pulse preceding that echo vector, is in the opposite quadrant (diametrically opposite) from the angle between a subsequent echo vector and its preceding refocusing pulse. The echoes having this relationship are said to have opposite ringing phase. For example, in FIG. 3, this relationship is caused to occur between echoes 1 and 3, echoes 2 and 4, echoes 5 and 7, and echoes 6 and 8, by changing the phases of the refocusing pulses appropriately. FIG. 3 in particular shows echo 1 in phantom in the plot for echo 3, and echo 2 in phantom in the plot for echo 4. The vectors for echo 1 and echo 3 are pointing in diametrically opposite directions, thus their ringing phases will cancel each other out when added. The same is true for echoes 2 and 4, echoes 5 and 7, and echoes 6 and 8. Thus by averaging within these pairs, the ringing of the refocusing pulses is cancelled. The resulting ring-free echo train is: (echo 1+echo 3)/2, (echo 2+echo 4)/2, (echo 5+echo 7)/2, (echo 6+echo 8)/2. Averaging over the whole cycle (echoes 1–8) also cancels the ringing.

The echoes that are to be added together can be in any sequential position in the refocusing sequence, or can span across refocusing sequences, depending on the phase of the refocusing pulses applied. In one implementation, the echoes that are added together are the nearest echoes having opposite ringing phase. What is important is that echoes are created in the train that have the aforementioned phase relationship with respect to at least one other prior or subsequent echo in the echo train. The magnitudes of the respective ringing-free echoes may be normalized prior to being added together.

One application for this ring cancellation scheme is fast NMR well logging sequences where short wait time measurements are combined with a long wait time measurement. To achieve fast logging speeds, the sequence is run in what is called in the art a "nonoverlapping mode," meaning that between two long wait time measurement the antenna is moved to a different part of the formation and thus might experience different ringing. If then the formation resistivity changes drastically between the two parts of the formation, the ringing will change and impact the cancellation of ringing by phase cycling. Thus, for these logging modes it will be advantageous to use the above-described ringing cancellation scheme. The loss of short T2 information due to averaging several echoes is not problematic if the long wait time XY8 measurement is combined with other short wait time measurements that provide this information anyway with higher signal-to-noise.

Figure 9:
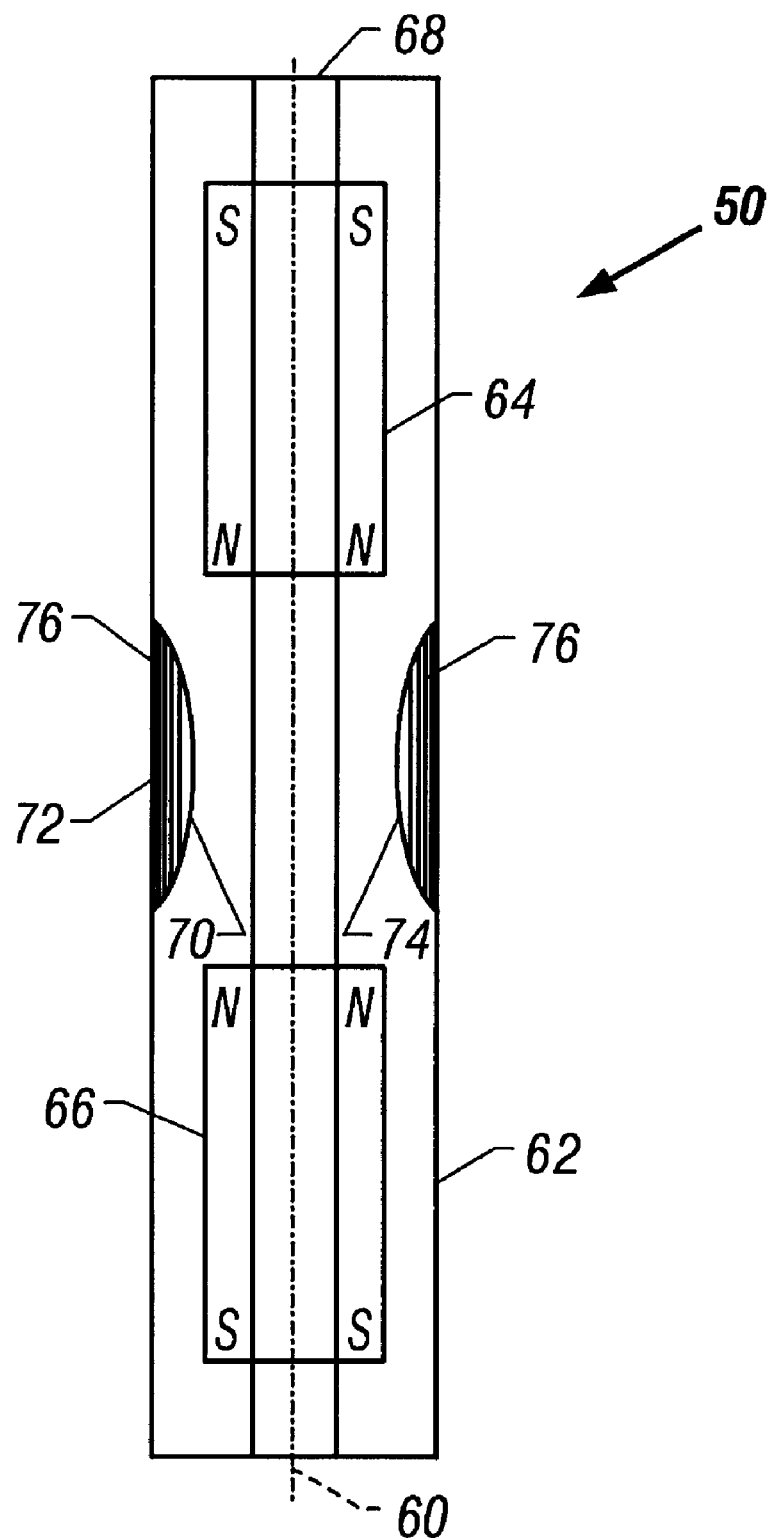
FIG. 9 is a diagram of an apparatus suitable for performing the processes shown in FIGS. 1 and 8.

FIG. 9 illustrates a nuclear magnetic resonance (NMR) logging-while-drilling tool 50 that may be used to perform the processes described above. The tool 50 has an axis 60 and can comprise a portion of a drill collar 62, which is substantially aligned with the axis of the wellbore. A static magnetic field is produced by tubular, axially polarized, permanent magnets 64, 66 that are mounted inside the drill collar 62. A channel 68 located inside the tool permits drilling mud to flow toward the drill bit. In the region between the magnets 64, 66, there is a recessed area 70. An RF antenna 72 is provided in the recessed area 70, which can be used for detecting NMR signals. However, a separate antenna or receiver may be used to detect the signals. A non-conductive material 74 can be provided in the recessed area 70 beneath the antenna 72. The material 74 may be a ferrite to increase the efficiency of the antenna 72. Alternatively, the material 74 may comprise a plastic, rubber, or a reinforced epoxy composite material.

Still referring to FIG. 9, in order to obtain azimuthal NMR measurements, at least one gradient coil 76 can be arranged in the recessed area 70. The geometry of the gradient coil 76 (e.g., a saddle coil) can produce a magnetic field around the tool 50. The magnetic field gradient will add to or subtract from the static magnetic field, depending on its azimuthal orientation to the gradient coil. Further details on the tool shown in FIG. 9 are disclosed in commonly assigned co-pending U.S. application Ser. No. 10/051,479, entitled Nuclear Magnetic Resonance Imaging Using Phase Encoding, to Krishnamurthy Ganesan, the entirety of which is incorporated herein by reference. The apparatus disclosed in U.S. Pat. No. 5,572,132 is also useful to impose magnetic field gradients for purposes of practicing the processes described herein.

While the invention has been particularly shown with reference to the above embodiments, it will be understood by those skilled in the art that various other changes in the form and details may be made therein without departing from the spirit and the scope of the invention.

What is claimed is:

1. A method for performing phase encoded inside-out magnetic resonance imaging, comprising steps of:
    (a) applying a static magnetic field in a volume of an earth formation surrounding a borehole which polarizes the nuclear spin within the volume of earth formation;
    (b) applying an excitation pulse into the formation that rotates the nuclear spin from a longitudinal axis of the static magnetic field to a plane transverse thereto;
    (c) applying a sequence of refocusing pulses a period of time after termination of the excitation pulse to generate a plurality of echoes;
    (d) detecting the echoes from the formation induced by each pulse in the sequence of refocusing pulses;
    (e) advancing the phase of the nuclear spin in the volume of earth formation by altering the magnetic field such that for a period of time, the strength of the magnetic field in the volume is spatially dependent;
    (f) repeating steps (c) through (e) until a desired number of echoes are obtained;
    (g) adding the echoes of each refocusing sequence to generate an average echo for each refocusing sequence; and
    (h) generating an image from the averaged echoes.

2. The method of claim 1, wherein the step (e) of advancing the phase of the nuclear spin comprises applying a magnetic field to impose a magnetic field gradient in a direction that is substantially orthogonal to the direction of the static magnetic field applied in step (a).

3. The method of claim 2, wherein the step (e) of advancing the phase of the nuclear spin comprises applying a magnetic field suitable to advance the phase of the nuclear spin by substantially the same amount for each iteration of refocusing pulse sequence.

4. The method of claim 3, wherein the step (h) of generating an image from the averaged echoes comprises performing a Fourier transformation on the averaged echoes to obtain an image.

5. The method of claim 1, and further comprising a step of applying an additional magnetic field to impose a magnetic gradient in the volume of earth formation in a direction different from a direction of the magnetic field applied in step (e).

6. The method of claim 5, wherein the step of applying the additional magnetic field is performed before the step (c) of applying a sequence of refocusing pulses.

7. The method of claim 1, wherein the step (c) of applying a sequence of refocusing pulses comprises applying a sequence of phase cycled CPMG refocusing pulses.

8. The method of claim 7, wherein the step (c) of applying a sequence of phase cycled CPMG refocusing pulses comprises applying an XY8 sequence.

9. The method of claim 1, wherein the step (c) of applying a sequence of refocusing pulses comprises applying a composite pulse sequence for each refocusing pulse, wherein the composite pulse sequence comprises multiple pulses.

10. The method of claim 1, wherein the step of applying an excitation pulse comprises applying an adiabatic half passage pulse sequence.

11. The method of claim 1, wherein steps (b) through (d) are applied with CPMG-like timing.

12. The method of claim 1, and further comprising steps of:
    adjusting the phase of each echo for delays between application of the refocusing pulse and detection of the subsequent echo;
    for the adjusted echoes, performing at least one mirroring operation about at least one axis in the transverse plane according to the phase of the refocusing pulses so that all the echoes obtained from a refocusing sequence have a common phase for that refocusing sequence.

13. The method of claim 12, wherein the step of adding comprises adding the common phase echoes to generate an average echo for each refocusing sequence.

14. A method for performing phase encoded inside-out magnetic resonance imaging, comprising steps of:
    (a) applying a static magnetic field in a volume of an earth formation surrounding a borehole which polarizes nuclear spin within the volume of earth formation;
    (b) applying an excitation pulse into the formation that rotates nuclear spin from a longitudinal axis of the static magnetic field to a plane transverse thereto;

(c) advancing the phase of the nuclear spin in the volume of earth formation by altering the magnetic field such that for a period of time, the strength of the magnetic field in the volume is spatially dependent;

(d) applying a sequence of refocusing pulses a period of time after termination of the excitation pulse to generate a plurality of echoes;

(e) detecting the echoes from the formation induced by each pulse in the sequence of refocusing pulses;

(f) repeating steps (d) and (e) until a desired number of echoes are obtained;

(g) adding the echoes of each refocusing sequence to generate an average echo for each refocusing sequence;

(h) repeating steps (a) through (g) until a desired number of phase advances are achieved; and (i) generating an image from the averaged echoes.

15. The method of claim 14, wherein the step (c) of advancing the phase of the nuclear spin comprises applying a magnetic field to impose a magnetic field gradient in a direction that is substantially orthogonal to the direction of the static magnetic field applied in step (a).

16. The method of claim 14, wherein the step (i) of generating an image from the averaged echoes comprises performing a Fourier transformation on the averaged echoes to obtain an image.

17. The method of claim 14, and further comprising a step of applying an additional magnetic field to impose a magnetic gradient in the volume of earth formation in a direction different from a direction of the magnetic field applied in step (c).

18. The method of claim 17, wherein the step of applying the additional magnetic field is performed between steps (e) and (f).

19. The method of claim 14, wherein the step (c) of applying a sequence of refocusing pulses comprises applying a sequence of phase cycled CPMG refocusing pulses.

20. The method of claim 19, wherein the step (c) of applying a sequence of phase cycled CPMG refocusing pulses comprises applying an XY8 sequence.

21. The method of claim 14, wherein the step (c) of applying a sequence of refocusing pulses comprises applying a composite pulse sequence for each refocusing pulse, wherein the composite pulse sequence comprises multiple pulses.

22. The method of claim 14, wherein the step of applying an excitation pulse comprises applying an adiabatic half passage pulse sequence.

23. The method of claim 14, wherein steps (b) through (e) are applied with CPMG-like timing.

24. The method of claim 14, and further comprising steps of:

adjusting the phase of each echo for delays between application of the refocusing pulse and detection of the subsequent echo;

for the adjusted echoes, performing at least one mirroring operation about at least one axis in the transverse plane according to the phase of the refocusing pulses so that all the echoes obtained from a refocusing sequence have a common phase for that refocusing sequence.

25. The method of claim 14, wherein the step (g) of adding comprises adding the common phase echoes to generate an average echo for each refocusing sequence.

26. A method for eliminating ringing while measuring a nuclear magnetic resonance property of a volume of earth formation surrounding a borehole, comprising steps of:

(a) applying a static magnetic field in a volume of an earth formation surrounding a borehole which polarizes the nuclear spin within the volume of earth formation;

(b) applying an excitation pulse into the formation that rotates the nuclear spin from a longitudinal axis of the static magnetic field to a plane transverse thereto;

(c) applying a sequence of refocusing pulses a period of time after termination of the excitation pulse to generate a plurality of echoes, comprising a step of changing the phase of pulses in the refocusing sequence so that pairs of echoes in the echo train have opposite ringing phase;

(d) detecting the echoes from the formation induced by each pulse in the sequence of refocusing pulses;

(e) repeating steps (c) and (d) until a desired number of echoes in an echo train are obtained;

(f) adding together echoes in the echo train that have opposite ringing phases to cancel ringing in the echo train; and (g) analyzing the resulting echo train for amplitude and/or decay characteristics.

27. The method of claim 26, wherein the step of applying a sequence of refocusing pulses comprises applying a sequence of phase cycled CPMG refocusing pulses.

28. The method of claim 26, wherein the step of applying a sequence of phase cycled CPMG refocusing pulses comprises applying an XY8 sequence.

29. The method of claim 28, wherein the step (g) comprises combining measurements for relatively long wait time phase cycled CPMG sequences with measurements from short wait time excitation pulses.

30. The method of claim 26, wherein the step (d) of detecting echoes is performed to obtain non-overlapping measurements of the formation from the borehole.

31. The method of claim 26, and further comprising the step of normalizing the amplitude of the echoes that are added together.

32. The method of claim 26, wherein the step (f) of adding comprises adding nearest echoes in the echo train having opposite ringing phase.

33. The method of claim 26, wherein the step of applying the refocusing pulse sequences comprises changing the phase of the refocusing pulses so that the angle between an echo vector and the rotation axis of its preceding refocusing pulse is diametrically opposite with respect to the angle between a subsequent echo vector and its preceding pulse.

34. The method of claim 26, and further comprising the step of, for each echo, performing at least one mirroring operation about at least one axis in the transverse plane according to the phase of the refocusing pulses so that all the echoes obtained from a refocusing sequence have a common phase for that refocusing sequence, prior to the step of adding.

* * * * *